(12) United States Patent
Duffer et al.

(10) Patent No.: US 10,052,265 B1
(45) Date of Patent: Aug. 21, 2018

(54) SPILL PROOF SPITOON

(71) Applicants: James E. Duffer, Bentonville, AR (US); David W. Richardson, Ash Grove, MO (US)

(72) Inventors: James E. Duffer, Bentonville, AR (US); David W. Richardson, Ash Grove, MO (US)

( * ) Notice: Subject to any disclaimer, the term of this patent is extended or adjusted under 35 U.S.C. 154(b) by 0 days.

(21) Appl. No.: 15/350,483

(22) Filed: Nov. 14, 2016

Related U.S. Application Data

(60) Provisional application No. 62/254,270, filed on Nov. 12, 2015.

(51) Int. Cl.
*A61J 19/00* (2006.01)
*A61J 19/02* (2006.01)
*A61L 2/23* (2006.01)

(52) U.S. Cl.
CPC ............... *A61J 19/02* (2013.01); *A61L 2/23* (2013.01)

(58) Field of Classification Search
CPC ............. A61J 19/00; A61J 19/02; A61L 2/23
USPC ............................ 4/261, 258, 267, 283, 248
See application file for complete search history.

(56) References Cited

U.S. PATENT DOCUMENTS

| | | | | |
|---|---|---|---|---|
| 199,541 A | * | 1/1878 | Heath | A61J 19/00 4/258 |
| 964,193 A | * | 7/1910 | Wagner | A61J 19/00 29/DIG. 97 |
| 1,091,418 A | * | 3/1914 | Woodworth | A61J 19/04 4/261 |
| 4,503,572 A | * | 3/1985 | Dawson | A61J 19/00 220/521 |
| 4,858,250 A | * | 8/1989 | Lee | A61J 19/00 4/258 |
| 4,908,882 A | * | 3/1990 | Williams | A61J 19/00 4/261 |
| 5,083,671 A | * | 1/1992 | Hayes | B65D 50/061 215/224 |
| D420,776 S | | 2/2000 | Lynch et al. | 34/2 |
| 6,305,033 B1 | * | 10/2001 | Azzam | A61J 19/00 220/738 |
| 6,491,993 B1 | * | 12/2002 | Forbes | B01J 20/28016 428/304.4 |
| 6,665,887 B2 | | 12/2003 | Nguyen | 4/258 |
| 6,718,563 B1 | * | 4/2004 | Kreiensieck | A61J 19/00 4/258 |
| 6,901,976 B1 | * | 6/2005 | Bautista | A61J 19/02 141/333 |
| 2006/0101564 A1 | * | 5/2006 | Powdermaker | A61J 19/00 4/259 |
| 2008/0295235 A1 | * | 12/2008 | Taras | A61J 19/00 4/271 |
| 2012/0047642 A1 | * | 3/2012 | Gedevanishvili | A61J 19/00 4/258 |
| 2016/0184187 A1 | * | 6/2016 | Brown | A61J 19/00 4/267 |

* cited by examiner

*Primary Examiner* — Benjamin R Shaw
(74) *Attorney, Agent, or Firm* — Keisling & Pieper PLC; David B. Pieper

(57) ABSTRACT

A spittoon constructed from a container including a tamper resistant seal, selectively operable flip top, absorbent medium having a masking odor, an adhesive property when wet, and extended antibacterial, antifungal, and/or germicidal properties.

2 Claims, 3 Drawing Sheets

SPILL PROOF SPITOON

CROSS-REFERENCE TO RELATED APPLICATIONS

This application claims priority to and is a continuation-in-part of U.S. Provisional Application Ser. No. 62/254,270 filed on Nov. 12, 2015 by Duffer and Richardson entitled Spill Proof Spitoon. Each of these applications are hereby incorporated by reference in their entirety.

STATEMENT REGARDING FEDERALLY SPONSORED RESEARCH OR DEVELOPMENT

Not Applicable.

REFERENCE TO A MICROFICHE APPENDIX

Not Applicable.

RESERVATION OF RIGHTS

A portion of the disclosure of this patent document contains material which is subject to intellectual property rights such as but not limited to copyright, trademark, and/or trade dress protection. The owner has no objection to the facsimile reproduction by anyone of the patent document or the patent disclosure as it appears in the Patent and Trademark Office patent files or records but otherwise reserves all rights whatsoever.

BACKGROUND OF THE INVENTION

1. Field of the Invention

The present invention relates to improvements in spittoons. More particularly, the invention relates to improvements particularly suited for providing a spill proof spittoon with a sticky and absorbent medium including antibacterial, antifungal, and/or germicidal properties. In particular, the present invention relates specifically to a container including a tamper resistant seal, selectively operable flip top, absorbent medium having a masking odor, an adhesive property when wet, and extended antibacterial, antifungal, and/or germicidal properties.

2. Description of the Known Art

As will be appreciated by those skilled in the art, spittoons are known in various forms. A spittoon has historically been a jar or vase set on the floor that is emptied on a regular basis. However, this has changed over the years such that now any old soda can, soda bottle or other container is now used as a portable spittoon. Patents disclosing information relevant to spittoons include: U.S. Pat. No. 4,858,250, issued to Lee on Aug. 22, 1989; U.S. D420,776, issued to Lynch et al. on Feb. 15, 2000; U.S. Pat. No. 6,665,887, issued to Nguyen on Dec. 23, 2003 entitled Portable Spittoon; and U.S. Pat. No. 6,718,563, issued to Kreiensieck on Apr. 13, 2000 entitled Spill proof spittoon cup. Each of these patents is hereby expressly incorporated by reference in their entirety.

From these prior references it may be seen that these prior art patents are very limited in their teaching and utilization, and an improved spittoon is needed to overcome these limitations.

SUMMARY OF THE INVENTION

The present invention is directed to an improved spittoon. In accordance with one exemplary embodiment of the present invention, a spittoon is provided using a container including a tamper resistant seal, selectively operable flip top, absorbent medium having a masking scent, an adhesive property when wet, and extended antibacterial, antifungal, and/or germicidal properties.

It is an object of this invention to provide a portable spittoon.

It is a further object of this invention to provide a spill proof spittoon.

Yet another object of the present invention is to provide a resealable spittoon.

A still further object of the present invention is to provide an extended shelf life spittoon.

A further object of the present invention is to ensure a tamper resistant spittoon.

A still further object of the present invention is for an aesthetically pleasing spittoon.

Another object of the present invention is to provide a spittoon capable of masking odors.

Yet another object of the present invention is to provide a spittoon with extended antibacterial, antifungal, and/or germicidal properties.

These and other objects and advantages of the present invention, along with features of novelty appurtenant thereto, will appear or become apparent by reviewing the following detailed description of the invention.

BRIEF DESCRIPTION OF THE SEVERAL VIEWS OF THE DRAWINGS

In the following drawings, which form a part of the specification and which are to be construed in conjunction therewith, and in which like reference numerals have been employed throughout wherever possible to indicate like parts in the various views.

DETAILED DESCRIPTION OF THE INVENTION

Figure 1:
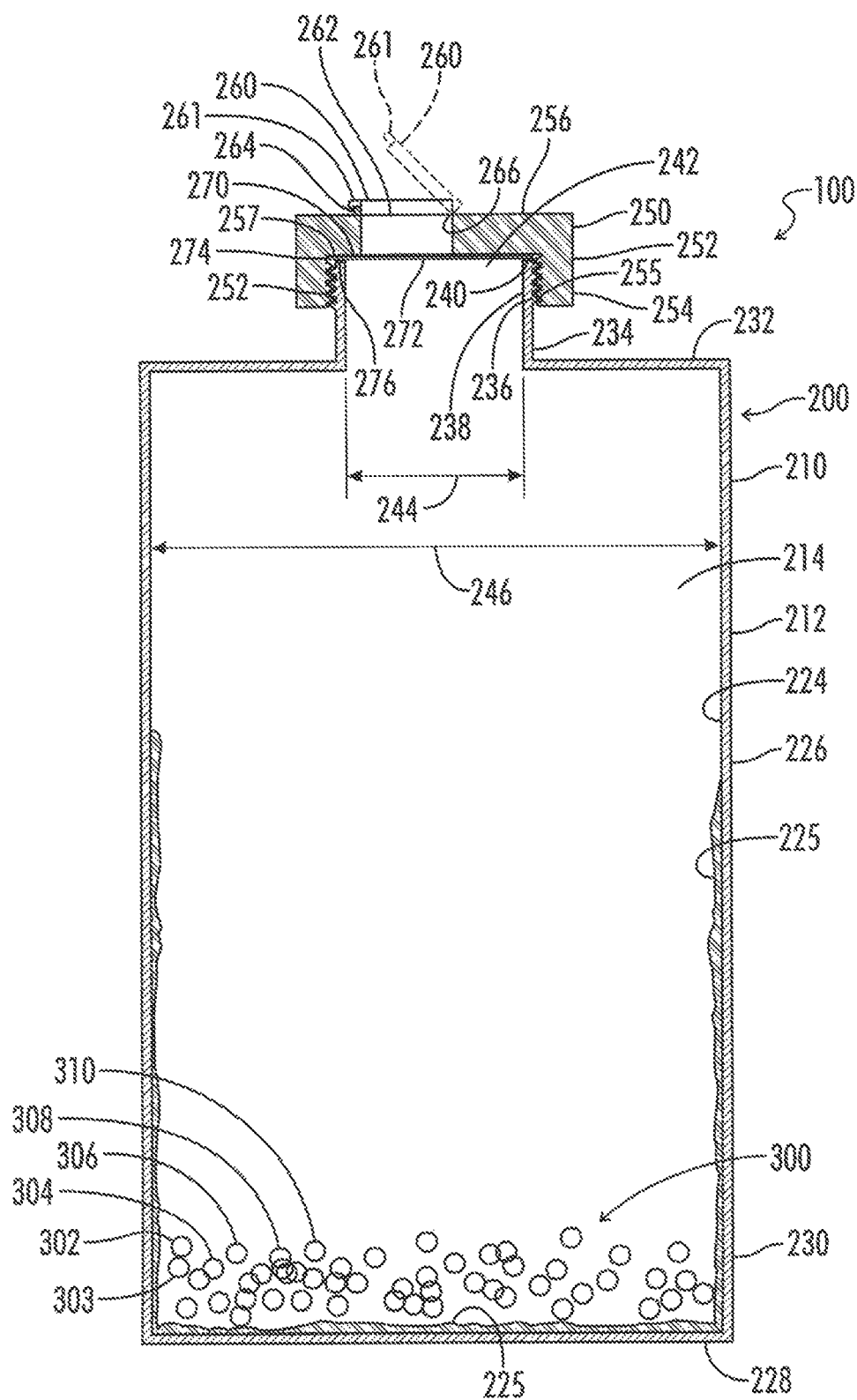
FIG. 1 is a schematic view of the present spittoon.
Figure 2:
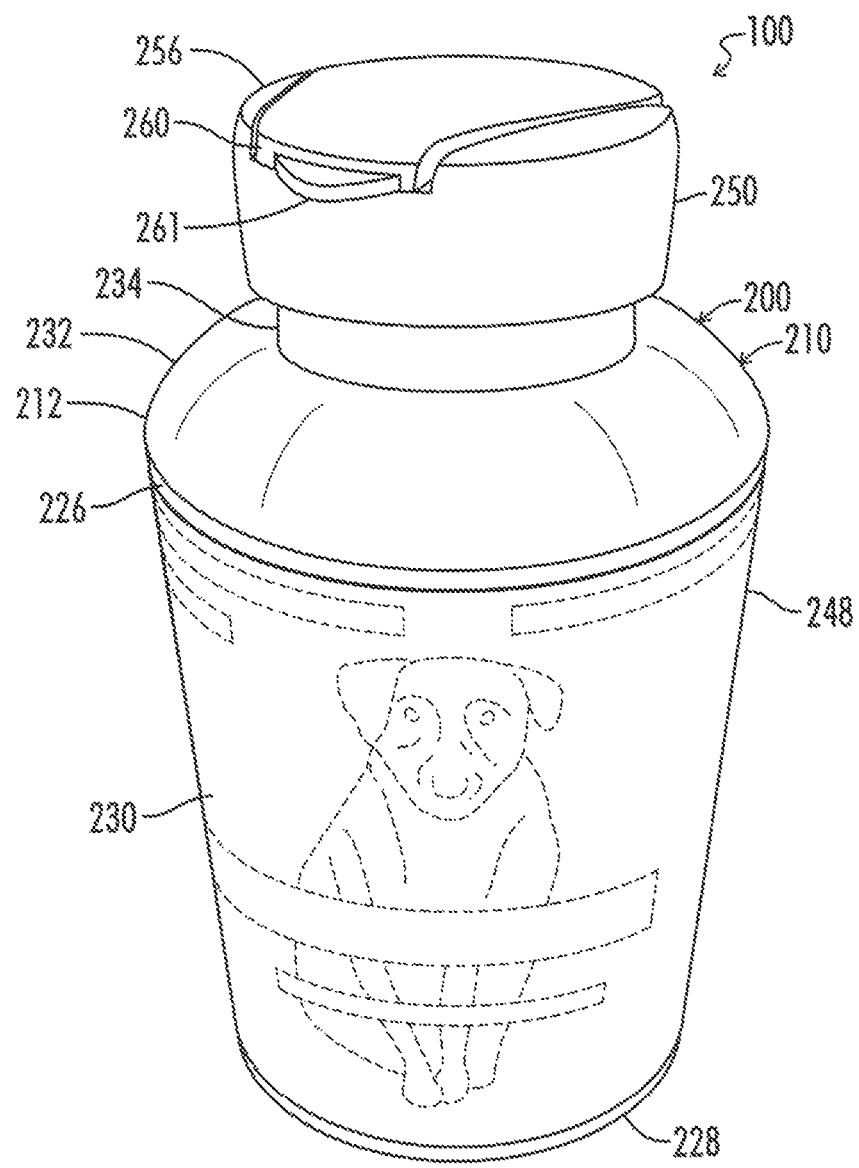
FIG. 2 is a perspective view of a preferred embodiment of the spittoon.
Figure 3:
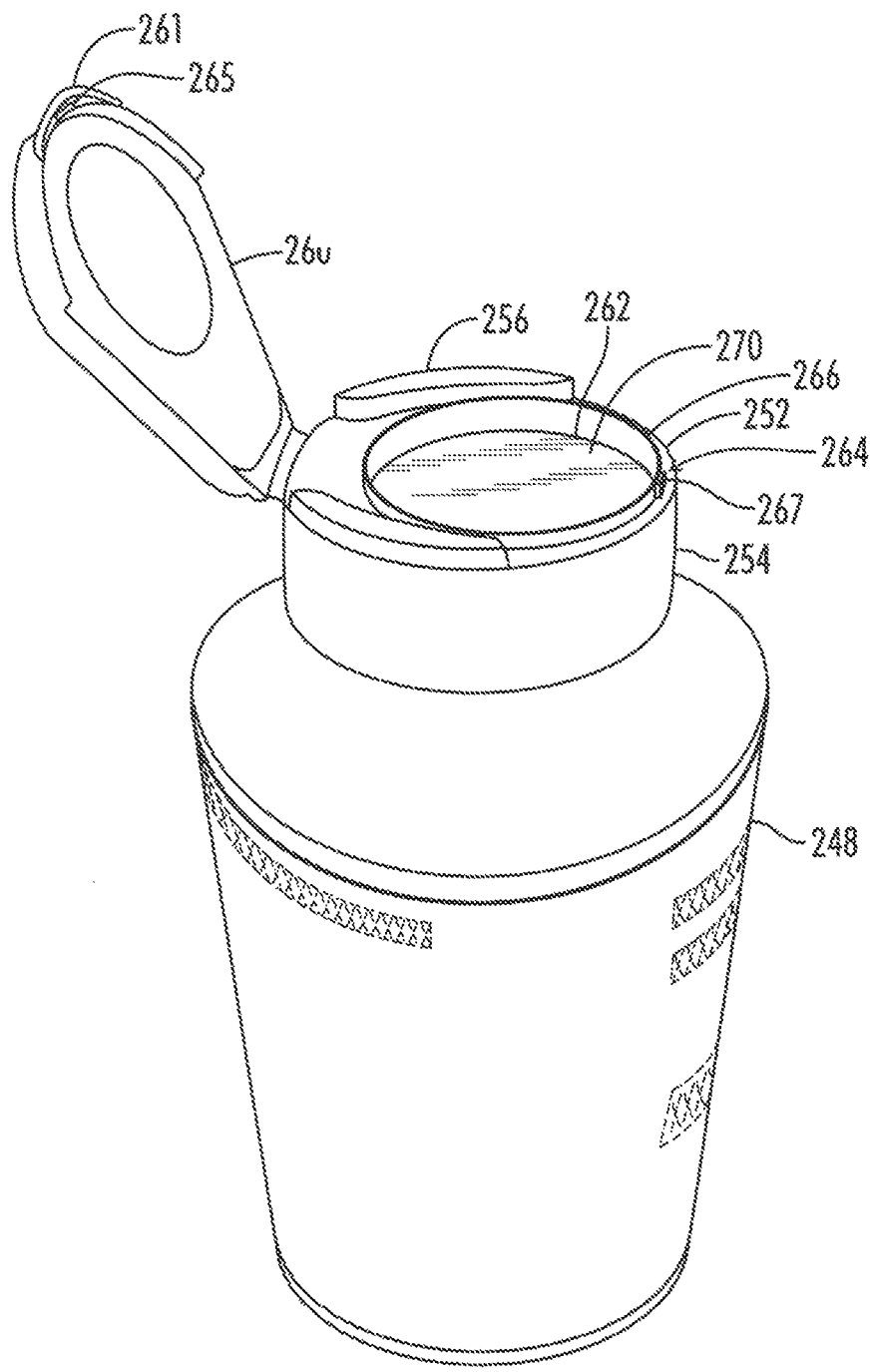
FIG. 3 is a perspective view of the preferred embodiment with the flip lid open.

As shown in FIGS. 1-3 of the drawings, one exemplary embodiment of the present invention is generally shown as a spittoon 100. The spittoon 100 is made with a container 200 including a container body 210, a label 248, a container top 250, and a spit contacting medium 300.

The container 200 is made with a container body 210 having a body wall 212. The body wall 212 defines an inner holding compartment 214 to contain the spit contacting medium 300. The inner holding compartment 214 is defines by the inner surface 224 of the body wall 212, and an opposing outer surface 226 is provided for holding by user and supporting the label 248. The inner surface 224 may have a texture 225 to enhance the ability of the spit contacting medium 300 to adhere to the inner surface 224 and remain in the container 100.

The container 200 includes a body bottom 228, body side 230, body shoulder 232, body neck 234, body threads 236, body top 238 and top rim 240. The body bottom also has an inner surface 224 that may include the texture 225. In the embodiment shown, the top rim 240 defines the body aperture 242. The top rim 240 is sealed to the safety seal 270 when the seal 270 is in place.

The container 200 also includes a container top 250. The container top 250 is constructed with a top body 252 including a side wall 254, top wall 256, top threads 255, and rim seat 257. The top threads 255 engage the body threads 236 to hold the container top 250 on the container body 210. The rim seat 257 sealably engages the top rim 240 once the safety seal 270 is removed and the container top 250 is installed on the container body 210.

The container top 250 further includes a flip lid 260. The flip lid 260 can be manipulated by the user by biasing the lid tab 261 to selectively access to the lid aperture 262. The lid aperture aligns with the body aperture 242. When the flip lid 260 is open with the safety seal 270 removed, the user may then deposit the spit into the lid aperture 262 where it drops to contact the spit contacting medium 300. The flip lid 260 is closed by pressing down on the lid tab 261 and the lid 260 is then held in a closed position by a selectively engageable lid lock 264 formed using a lid tab 261 against a lid recess 265. When the flip lid 260 is in the locked position and the lid lock 264 is engaged, a lid seal 266 flowably blocks the lid aperture 262.

A safety seal 270 is provided across the top rim 240 to seal the spit contacting medium 300 in the inner compartment 214 before use. The safety seal 270 is made with a continuous membrane 272 that is immoveable by pulling on the membrane tab 274 to break the membrane seal 276.

The spit contacting medium 300 is made with an absorbent medium 302 and binding agent 303. Once the absorbent medium 302 and binding agent 303 are contacted by spit, the absorbent medium 302 has an adhesive property such that it adheres to the inner surface 224. The absorbent medium 302 and binding agent 303 should be selected such that the adhesive property of the medium 302 at least exceeds the force of gravity on a full container of spit to provide a spill proof feature to the invention. In the embodiment described here, the absorbent medium 302 and binding agent 303 have a combined adhesive property greater than the force of gravity such that when the container 100 is inverted and shaken, neither the absorbed spit, nor any of the spit contacting medium 300 leaves the inner holding compartment 214. Note also that body aperture distance 244 is smaller than the body compartment distance 246 such that this allows the gel like nature of the spit contacting medium 300, usually referred to as having the properties of low viscosity or a high shearing force of the spit contacting medium 300, to be used in addition to the frictional force for holding the spit absorbing medium in the container 200. This provides additional assurance of spill resistance when the container 200 is shaken.

The spit contacting medium 300 is enhanced past the absorbent medium 302 and the binding agent 303 with an aroma medium 304, antibacterial medium 306, antifungal medium 308, and germicidal medium 310. For a 20 oz container 200, approximately 10 grams of spit contacting medium 300 is used with the majority being the absorbent medium 302 with approximately three percent binding agent 303 and the remainder being the aroma medium 304, antibacterial medium 306, antifungal medium 308, and germicidal medium 310. Note that the invention can be greatly varied over a broad range of concentrations of these materials such that this invention is not meant to be limited to this particular concentration level, instead, the concentrations should only be limited by the important properties provided by each. Thus, a one percent absorbent medium 302, one percent binding agent 303 and ninety eight percent aroma medium 304, antibacterial medium 306, antifungal medium 308, and germicidal medium 310 can provide features of this invention. Similarly, a one percent absorbent medium 302, ninety eight percent binding agent 303 and one percent aroma medium 304, antibacterial medium 306, antifungal medium 308, and germicidal medium 310 can provide features of this invention. In this manner, we note that variation to the teachings of this invention are within the invention taught herein. For the preferred embodiment, we provide the following detail on the materials selected for each aspect of the invention.

The absorbent medium 302 is Na Polyacrylate commonly known as waterlock which is a sodium salt of polyacrylic acid with the chemical formula $[-CH_2-CH(CO_2Na)-]n$. The absorbent medium 302 has the ability to absorb as much as 200 to 300 times its mass in water. The amount used in the medium 300 should be selected to quickly absorb the spit, without allowing the expanded absorbent medium 302 to exceed the volume of the container.

The binding agent 303 is bentonite, basically an impure clay that acts both as a binding agent or caking agent, and also provides absorbent properties. The ionic surface of bentonite has a useful property in making a sticky coating to make the medium 300 adhere to the inner surface 224. Bentonite also has the property of absorbing protein molecules from aqueous solutions. Because bentonite swells when contacted with moisture, bentonite useful in providing a self-sealing, low-permeability barrier and its absorbent properties also help to increase shelf life by acting as a desiccant. As previously noted, the quantity of bentonite should be selected to such that the adhesive property of the medium 302 at least exceeds the force of gravity to provide a spill proof feature to the invention and is preferably of sufficient concentration to hold the absorbed spit in the container 100 when it is inverted and lightly shaken.

The aroma medium 304, antibacterial medium 306, antifungal medium 308, and germicidal medium 310 are each provided by the use of menthol. Menthol provides a smell that is known to be pleasant to most people for the aroma medium 304. Menthol also provides the antibacterial, antifungal, and germicidal properties. Basically, a sufficient amount of menthol should be selected so that the aroma is detectable but is not overpowering to the user. Once this level is achieved, the quantity of menthol is sufficient to provide the antibacterial, antifungal, and germicidal properties because of the constant contact with the absorbed spit. This is not an application where it is necessary to quickly provide these features such as in a skin cream, but is instead a long-term exposure in a sealed container.

Reference numerals used throughout the detailed description and the drawings correspond to the following elements:

Spittoon 100
Container 200
  Container body 210
    Body wall 212
      Inner holding compartment 214
      Inner surface 224
      Outer surface 226
      Body bottom 228
      Body side 230
      Body shoulder 232
      Body neck 234
      Body threads 236
      Body top 238
      Top rim 240
      Body aperture 242

Body aperture distance 244
Body compartment distance 246
Container top 250
  Top body 252
    Side wall 254
    Top threads 255
    Top wall 256
    Rim seat 257
  Flip lid 260
    Lid tab 261
    Lid aperture 262
    Lid lock 264
    Lid recess 265
    Lid seal 266
    Lid tab 267
  Safety seal 270
    Continuous membrane 272
    Membrane tab 274
    Membrane seal 276
Spit contacting medium 300
  Absorbent medium 302
  Binding agent 303
  Aroma medium 304
  Antibacterial medium 306
  Antifungal medium 308
  Germicidal medium 310

From the foregoing, it will be seen that this invention well adapted to obtain all the ends and objects herein set forth, together with other advantages which are inherent to the structure. It will also be understood that certain features and subcombinations are of utility and may be employed without reference to other features and subcombinations. This is contemplated by and is within the scope of the claims. Many possible embodiments may be made of the invention without departing from the scope thereof. Therefore, it is to be understood that all matter herein set forth or shown in the accompanying drawings is to be interpreted as illustrative and not in a limiting sense.

When interpreting the claims of this application, method claims may be recognized by the explicit use of the word 'method' in the preamble of the claims and the use of the 'ing' tense of the active word. Method claims should not be interpreted to have particular steps in a particular order unless the claim element specifically refers to a previous element, a previous action, or the result of a previous action. Apparatus claims may be recognized by the use of the word 'apparatus' in the preamble of the claim and should not be interpreted to have 'means plus function language' unless the word 'means' is specifically used in the claim element. The words 'defining,' 'having,' or 'including' should be interpreted as open ended claim language that allows additional elements or structures. Finally, where the claims recite "a" or "a first" element of the equivalent thereof, such claims should be understood to include incorporation of one or more such elements, neither requiring nor excluding two or more such elements.

What is claimed is:

1. A spill resistant spittoon apparatus for use in holding a user's spit inside the spittoon with a force greater than the force of gravity, comprising:
    a container including a container body, a container top, and a spit contacting medium;
    the container body having a body wall defining an inner holding compartment with an inner surface;
    the container body defining a body aperture;
    the container top having a top body defining a lid aperture flowably aligned with the body aperture;
    the spit contacting medium including an absorbent medium and a binding agent;
    the spit contacting medium having a frictional engagement with the inner surface exceeding the force of gravity after absorbing the user's spit; and
    the binding agent including bentonite.

2. A spill resistant spittoon apparatus for use in holding a user's spit inside the spittoon with a force greater than the force of gravity, comprising:
    a container including a container body, a container top, and a spit contacting medium;
    the container body having a body wall defining an inner holding compartment with an inner surface;
    the container body defining a body aperture;
    the container top having a top body defining a lid aperture flowably aligned with the body aperture;
    the spit contacting medium including an absorbent medium and a binding agent;
    the spit contacting medium having a frictional engagement with the inner surface exceeding the force of gravity after absorbing the user's spit;
    the container body defining a body aperture smaller than a body diameter;
    the container top including a flip lid;
    the flip lid including a lid tab;
    the flip lid including a lid lock;
    a safety seal positioned between the container body and the container top;
    the absorbent medium including Na Polyacrylate;
    the binding agent including bentonite;
    the spit contacting medium further including menthol.

\* \* \* \* \*